United States Patent
Watanabe

[11] Patent Number: 5,856,621
[45] Date of Patent: Jan. 5, 1999

[54] ELASTIC MODULUS DETERMINATION OF COMPOSITE MATERIAL

[75] Inventor: Yohsuke Watanabe, Tokyo, Japan

[73] Assignee: NEC Corporation, Tokyo, Japan

[21] Appl. No.: 807,693

[22] Filed: Feb. 28, 1997

[30] Foreign Application Priority Data

Feb. 29, 1996 [JP] Japan ................................ 8-069483

[51] Int. Cl.$^6$ .................................................. G01D 1/16
[52] U.S. Cl. .............................................. 73/789; 73/772
[58] Field of Search ........................... 73/789, 791, 792, 73/597, 159, 772; 364/559

[56] References Cited

U.S. PATENT DOCUMENTS

| | | | |
|---|---|---|---|
| 3,948,091 | 4/1976 | Voll | 73/772 |
| 5,297,062 | 3/1994 | Cresson et al. | 73/159 |
| 5,408,882 | 4/1995 | McKinley et al. | 73/597 |
| 5,649,448 | 7/1997 | Koskimies et al. | 73/862.451 |

FOREIGN PATENT DOCUMENTS 5-223711  8/1993  Japan .

*Primary Examiner*—Max H. Noori
*Attorney, Agent, or Firm*—Sughrue, Mion, Zinn, Macpeak & Seas, PLLC

[57] ABSTRACT

An elastic modulus of an element of a material including fibers in a selected direction is determined as follows. First, a parallel elastic modulus, an orthogonal elastic modulus and fiber orientation of the material are stored. The elastic modulus of the element is determined based on the first elastic modulus, the second elastic modulus and an angle between the fiber orientation of the element and the selected direction such that the elastic modulus is determined as a function of the angle between the fiber orientation of the element and the selected direction when the selected direction is neither parallel nor orthogonal to the fiber orientation of the element.

20 Claims, 6 Drawing Sheets

PARALLEL MODULUS A

ORTHOGONAL MODULUS B

FIG. 4
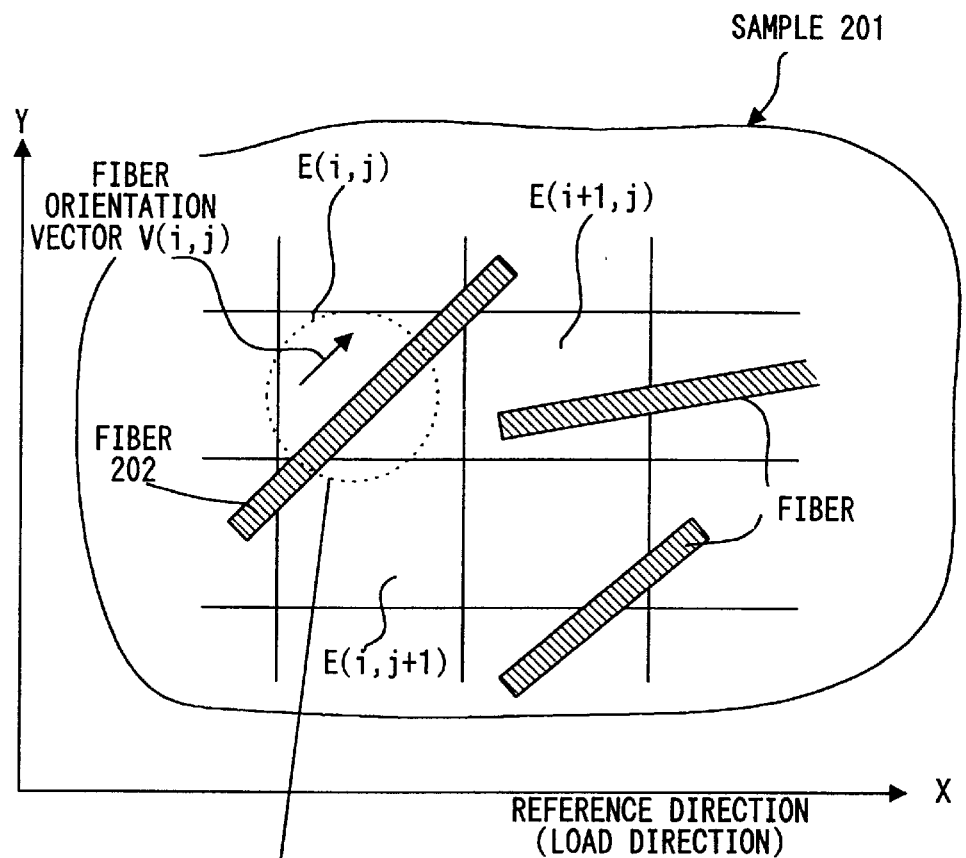
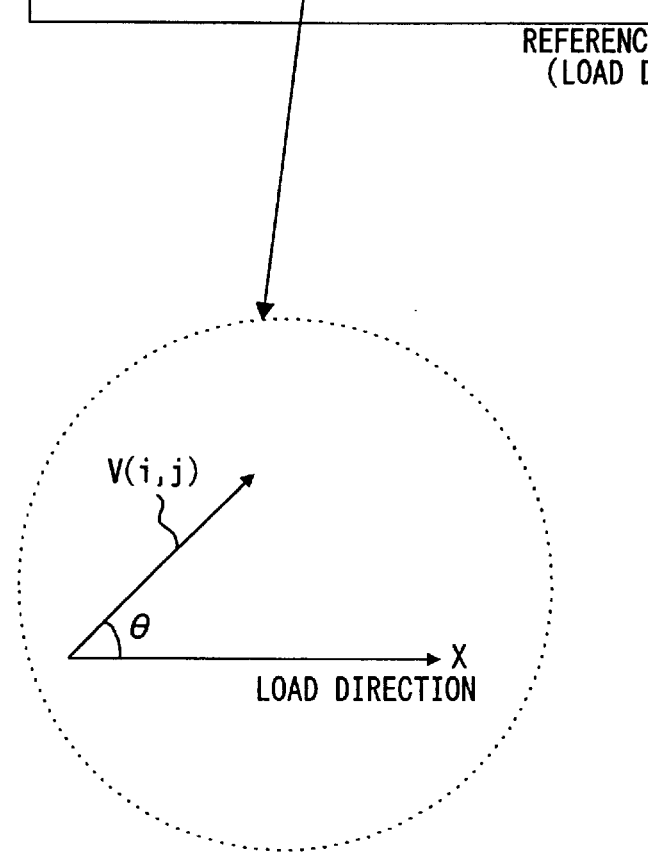

ELASTIC MODULUS DETERMINATION OF COMPOSITE MATERIAL

BACKGROUND OF THE INVENTION

1. Field of the invention

The present invention generally relates to structural analysis of materials and, in particular to an elastic modulus determination method of a composite material including fibers.

2. Description of the Related Art

There has been proposed a three-dimensional structural analysis method in Japanese Patent Unexamined Publication No. 5-223711 using a finite element method of a honeycomb structure model to analyze the mechanical characteristics of synthetic resin foam when an impact deformation occurs. According to this method, a stress component corresponding to a strain component in each direction can be calculated using the same maximum stress-strain curve. This allows the honeycomb structure model to be treated as a structural model having isotropic mechanical characteristics similar to an actual synthetic resin foam.

SUMMARY OF THE INVENTION

The conventional method, however, cannot be applied to structural analysis of fiber reinforced composites or fiber reinforced plastics. The reason is that the fiber orientation and the resin flow make a difference in elastic modulus among the elements, resulting in increased analysis error. Further, it is difficult to predict a variation of elastic modulus caused by the fiber orientation and the resin flow.

An object of the present invention is to provide a method of accurately determining the elastic modulus of each element in a composite material including fibers.

Another object of the present invention is to provide a method of setting the elastic modulus of a composite material including fibers so as to allow the structural analysis of a close-to-real composite material.

According to the present invention, an elastic modulus of an element of a material including fibers in a desired direction is determined by the following step. First, a first elastic modulus, a second elastic modulus and fiber orientation of the material are stored. The first elastic modulus is an elastic modulus of the material in a direction parallel to the fiber orientation and the second elastic modulus is an elastic modulus of the material in a direction orthogonal to the fiber orientation. The elastic modulus of the element is determined based on the first elastic modulus, the second elastic modulus and an angle between the fiber orientation of the element and the desired direction.

The elastic modulus of each element of a plurality of elements representing the material may be determined by selecting the element one by one from the elements until all the elements are selected. The respective elastic moduli of the material may be used for structural analysis of the material. Further, the fiber orientation of the material can be obtained based on flow simulation of molten material including the fibers flowing into a mold.

The elastic modulus of the element may be determined so that the first elastic modulus is determined as the elastic modulus of the element when the reference direction is parallel to the fiber orientation of the element, the second elastic modulus is determined as the elastic modulus of the element when the reference direction is orthogonal to the fiber orientation of the element, and the elastic modulus of the element is determined as a function of the angle between the fiber orientation of the element and the reference direction when the desired direction is neither parallel nor orthogonal to the fiber orientation of the element.

BRIEF DESCRIPTION OF THE DRAWINGS

FIG. 4 is a schematic diagram showing an example of the composite material including fibers in the case of the load direction being setting to the X axis;

DETAILED DESCRIPTION OF THE PREFERRED EMBODIMENTS

Figure 1:
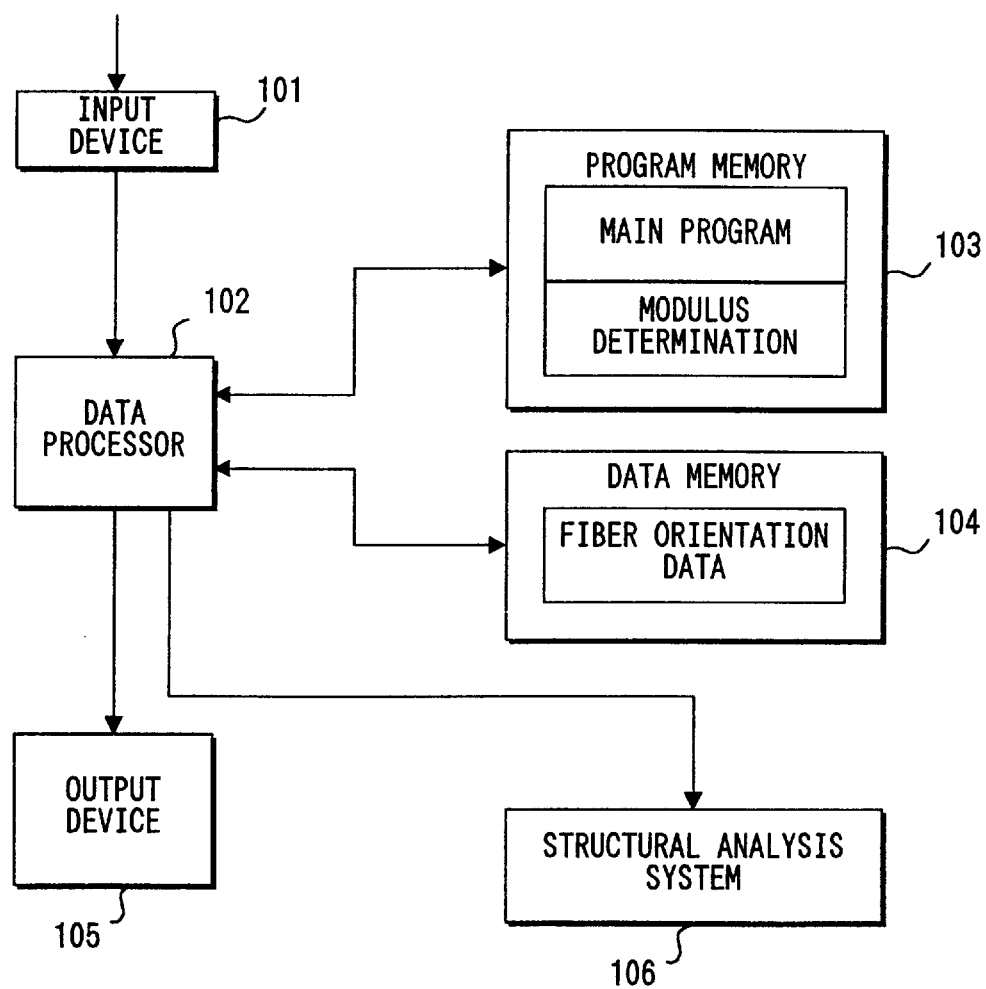
FIG. 1 is a block diagram showing an embodiment of an elastic modulus determination system according to the present invention.

Referring to FIG. 1, an elastic modulus determination system is provided with an input device 101 such as a keyboard and a pointing device, which is used to input necessary data, for instance, a parallel modulus and an orthogonal modulus. Modulus determination is performed by a program-controlled data processor 102 according to a main program and a modulus determination program which are previously stored in a program memory 103. Necessary data for the modulus determination such as fiber orientation vector data is stored in a data memory 104. The fiber orientation vector data is obtained by flow simulation of molten resin including fibers, which will be described hereinafter. A output device 105 is a display and a printer, for instance. The elastic modulus obtained by this system is supplied to a structural analysis system 106. Needless to say, the structural analysis system 106 may be implemented by the data processor 102 using a structural analysis program.

FIBER ORIENTATION

In general, when the molten resin including fibers flows into a metal mold, the fibers are supposed to be approximately oriented in lines of flow. Therefore, the fiber orientation data can be obtained by the flow simulation of molten resin including fibers. The flow simulation may be implemented by the data processor 102 using a flow simulation program.

Figure 2:
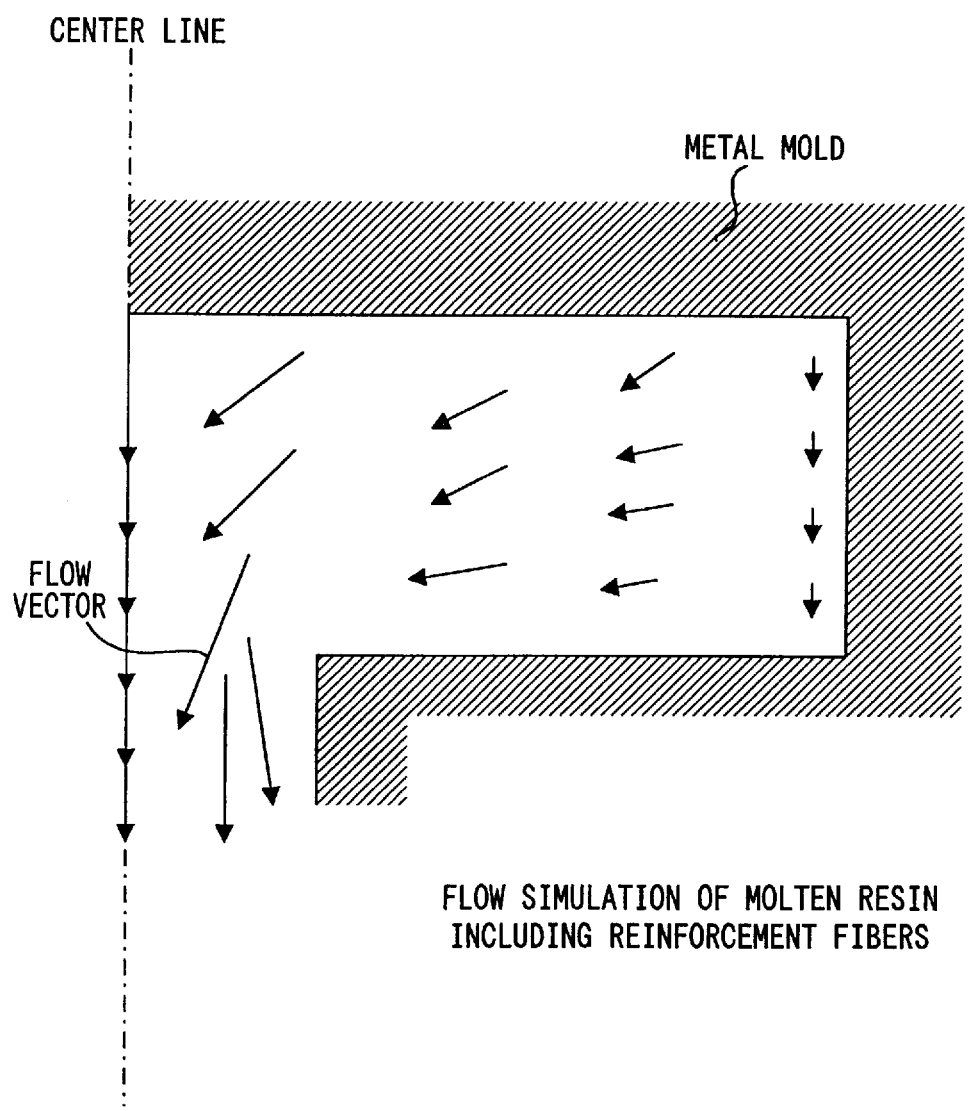
FIG. 2 is a schematic diagram showing a flow simulation of molten plastics including fibers to obtain the fiber orientation.

Referring to FIG. 2, in the case where the molten resin including fibers flows into a T-shaped metal mold, the computer simulation of flow shows flow vectors at the different positions within the metal mold as shown in the figure. Using the resultant flow vectors, the approximate fiber orientation can be obtained.

REFERENCE MODULUS

Figure 3A:
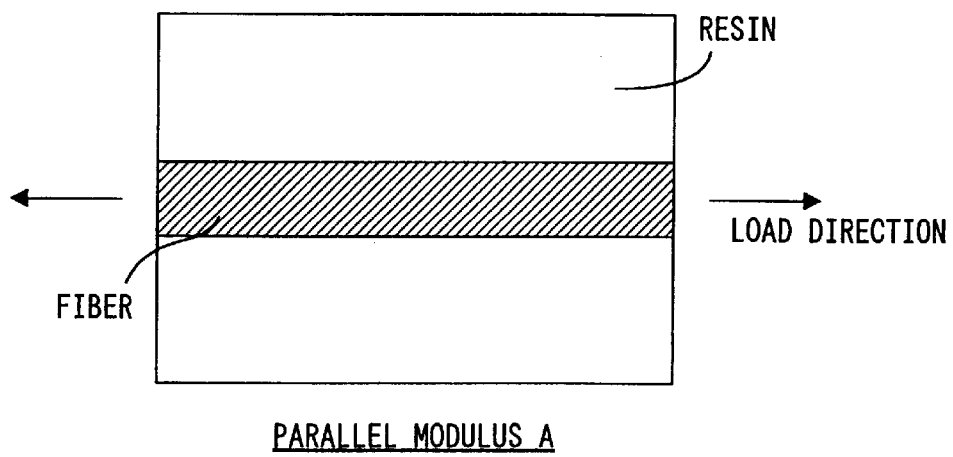
FIG. 3A is a schematic diagram showing a composite material including a fiber which is loaded in a direction parallel to the fiber to obtain a parallel modulus A.
Figure 3B:
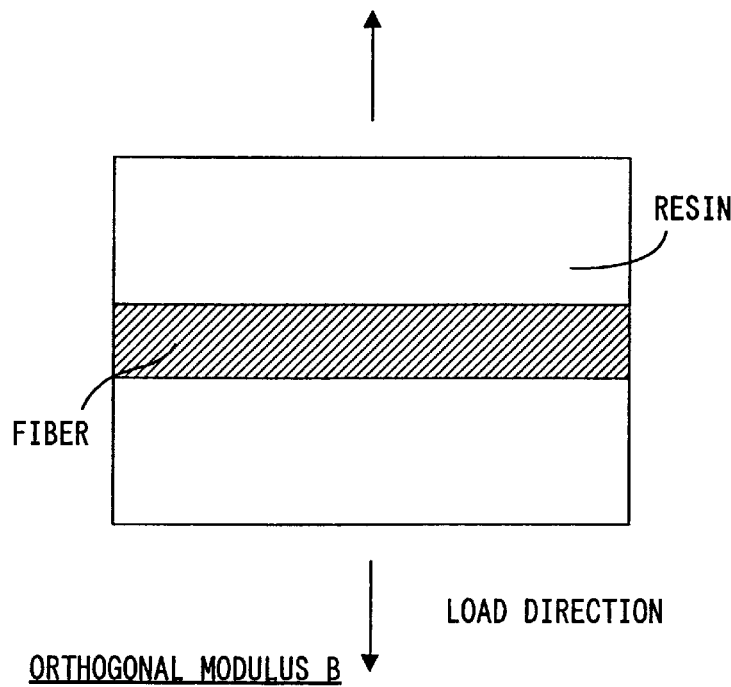
FIG. 3B is a schematic diagram showing a composite material including a fiber which is loaded in a direction orthogonal to the fiber to obtain an orthogonal modulus B.

It is known that the resin including reinforcement fibers has isotropic elastic modulus. In the embodiment, two reference moduli, that is, a parallel modulus A and an orthogonal modulus B are used to determine the elastic modulus of each element in the resin including reinforcement fibers. The parallel modulus A is obtained by loading the resin including oriented fibers in the direction parallel to the fiber orientation as shown in FIG. 3A. On the other hand, the orthogonal modulus B is obtained by loading the resin including oriented fibers in the direction orthogonal to the fiber orientation as shown in FIG. 3B. The parallel modulus A and the orthogonal modulus B are input as reference moduli through the input device 101.

MODULUS DETERMINATION

Referring to FIG. 4, it is assumed that a synthetic resin sample 201 including fibers 202 are divided into m×n elements each indicating E(i, j), where $1 \leq i \leq m$ and $1 \leq j \leq n$. The fiber orientation vector V(i, j) of each element E(i, j) is obtained by the flow simulation as described above and is stored in the data memory 104. Further assuming that the synthetic resin sample 201 is loaded in the direction X, the modulus determination procedure will be described hereinafter.

Figure 5:
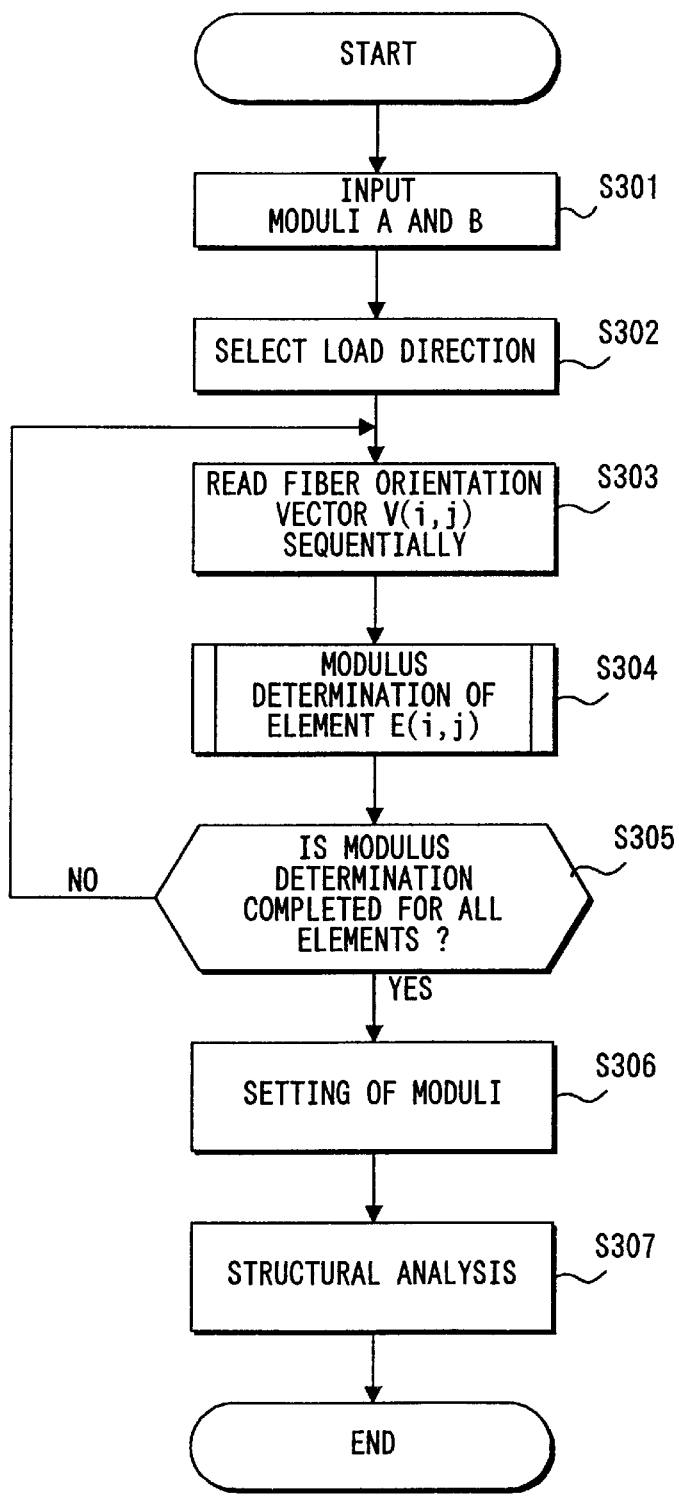
FIG. 5 is a flowchart showing an embodiment of a modulus setting method according to the present invention.

Referring to FIG. 5, the parallel modulus A and the orthogonal modulus B are input through the input device 101 (step S301), and then the load direction is set to the x axis as shown in FIG. 4 (step S302). Subsequently, the data processor 102 reads the fiber orientation vector v(i, j) of an element E(i, j) from the data memory 104 (step S303). The modulus of the element E(i, j) is determined based on the parallel modulus A, the orthogonal modulus B and the fiber orientation vector V(i, j) (step S304). The steps S303 and S304 are repeated while incrementing i and j until the modulus determination is completed for all elements (step S305). In this manner, the elastic moduli of the m×n elements are calculated and stored into the data memory 104 (step S306). The m×n elastic moduli of the synthetic resin sample 201 are output to the structural analysis system 106 (step S307). The details of the modulus determination step S304 will be described hereinafter.

Figure 6:
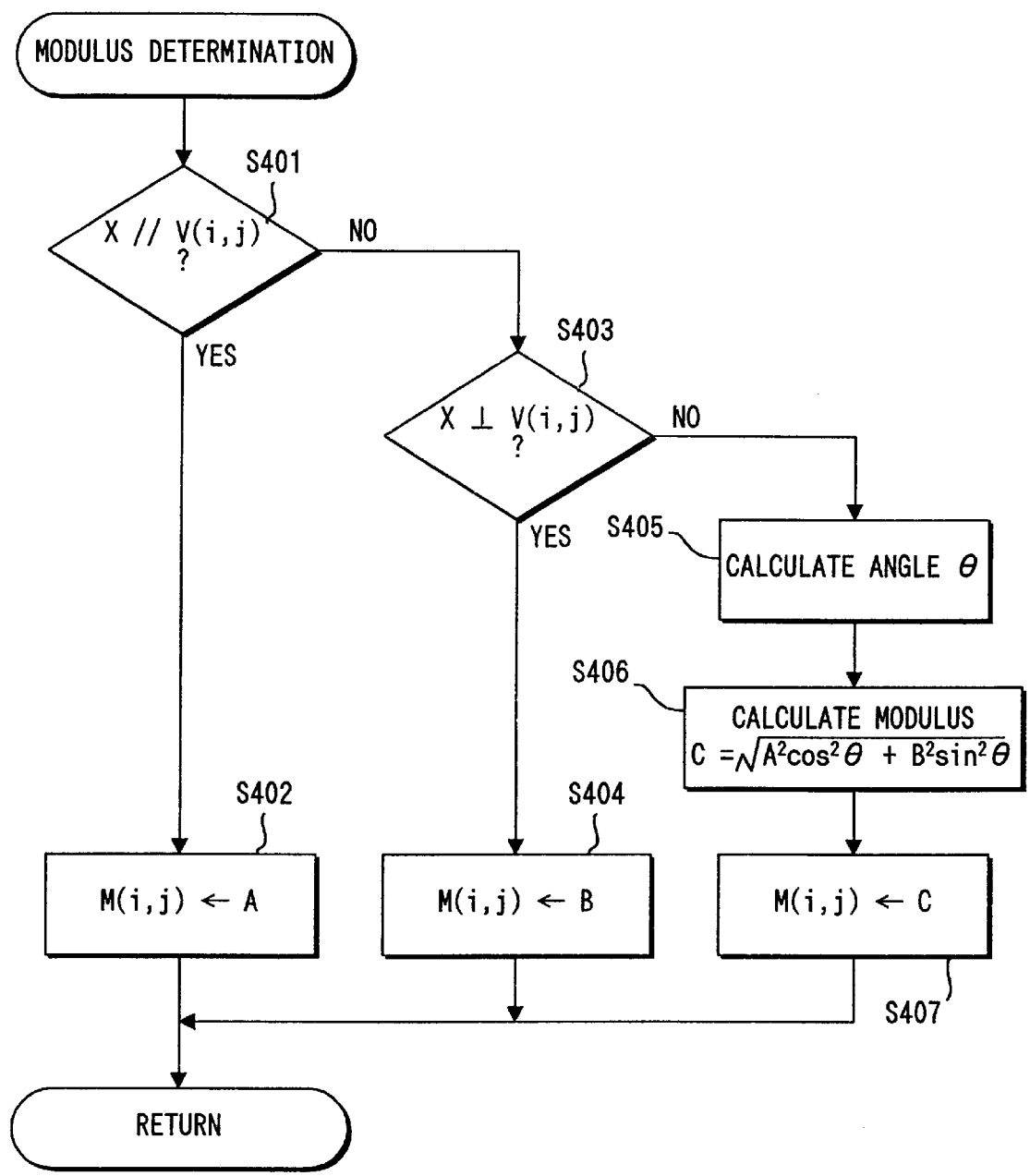
FIG. 6 is a flowchart showing a modulus calculation method of an element in the embodiment of FIG. 5.

Referring to FIG. 6, when the fiber orientation vector V(i, j) of an element E(i, j) is read from the data memory 104, it is checked whether the fiber orientation vector V(i, j) is parallel to the load direction, that is, the X axis (step S401). When they are parallel (YES of step S401), the elastic modulus M(i, j) of an element E(i, j) is set to the parallel modulus A (step S402). When the fiber orientation vector V(i, j) is not parallel to the load direction (NO of step S401), it is checked whether the fiber orientation vector V(i, j) is orthogonal to the load direction (step S403). When they are orthogonal (YES of step S403), the elastic modulus M(i, j) of an element E(i, j) is set to the orthogonal modulus B (step S404). When the fiber orientation vector V(i, j) is neither parallel nor orthogonal to the load direction (NO of step S403), the angle θ between the fiber orientation vector V(i, j) and the load direction (X) is calculated as shown in FIG. 4 (step S405). Subsequently, an elastic modulus C is calculated using the following equation:

$$C = \sqrt{A^2\cos^2\theta + B^2\sin^2\theta} \text{ (step S406), and}$$

the elastic modulus M(i, j) of an element E(i, j) is set to the calculated modulus C (step S407).

As described above, since the elastic modulus of an element is determined using the fiber orientation data, the accurate modulus of each element can be obtained, result in allowing the structural analysis of a close-to-real composite material.

What is claimed is:

1. An electronic computer system for determining an elastic modulus of each element of a plurality of elements representing a material including fibers, comprising:
an input device for inputting a first elastic modulus and a second elastic modulus, the first elastic modulus being an elastic modulus of the material in a direction parallel to the fiber orientation, the second elastic modulus being an elastic modulus of the material in a direction orthogonal to the fiber orientation;
a data memory for storing fiber orientation of each element of the material; and
a processor for determining the elastic modulus of each element based on the first elastic modulus, the second elastic modulus and an angle between the fiber orientation of the element and a desired loading direction.

2. The electronic computer system according to claim 1, wherein the processor sequentially selects an element from the elements and determines the elastic modulus of a selected element until all the elements are selected.

3. The electronic computer system according to claim 2, wherein the processor stores the elastic modulus of each element of the material onto the data memory for use in structural analysis of the material.

4. The electronic computer system according to claim 1, wherein the fiber orientation of the material is obtained based on flow simulation of molten material including the fibers flowing into a mold.

5. The electronic computer system according to claim 1, wherein the processor determines the first elastic modulus as the elastic modulus of the element when the desired direction is parallel to the fiber orientation of the element, determines the second elastic modulus as the elastic modulus of the element when the desired direction is orthogonal to the fiber orientation of the element, and determines the elastic modulus of the element as a function of the angle between the fiber orientation of the element and the desired direction when the desired direction is neither parallel nor orthogonal to the fiber orientation of the element.

6. The electronic computer system according to claim 5, wherein the elastic modulus of the element is determined using the following equation:

$$C = \sqrt{A^2\cos^2\theta + B^2\sin^2\theta}\ ,$$

where C is the elastic modulus of the element, A is the first elastic modulus, B is the second elastic modulus, and θ is the angle between the fiber orientation of the element and the desired direction.

7. The electronic computer system according to claim 3, wherein the processor performs the structural analysis of the material.

8. The electronic computer system according to claim 4, wherein the processor performs the flow simulation.

9. An electronic computer implemented method for determining an elastic modulus of each element of a plurality of elements representing a material including fibers, comprising the steps of:
storing fiber orientation of each element of the material;
inputting a first elastic modulus and a second elastic modulus, the first elastic modulus being an elastic modulus of the material in a direction parallel to the fiber orientation, the second elastic modulus being an elastic modulus of the material in a direction orthogonal to the fiber orientation;

selecting a reference direction; and determining the elastic modulus of each element so that the first elastic modulus is determined as the elastic modulus of the element when the reference direction is parallel to the fiber orientation of the element, the second elastic modulus is determined as the elastic modulus of the element when the reference direction is orthogonal to the fiber orientation of the element, and the elastic modulus of the element is determined as a function of the angle between the fiber orientation of the element and the reference direction when the desired direction is neither parallel nor orthogonal to the fiber orientation of the element.

10. The electronic computer implemented method according to claim 9, wherein the elastic modulus of the element is determined using the following equation:

$$C = \sqrt{A^2\cos^2\theta + B^2\sin^2\theta} \quad,$$

where C is the elastic modulus of the element, A is the first elastic modulus, B is the second elastic modulus, and $\theta$ is the angle between the fiber orientation of the element and the reference direction.

11. A electronic computer memory storing a program for determining an elastic modulus of each element of a plurality of elements representing a material including fibers, the program comprising the steps of:

storing fiber orientation of each element of the material;

inputting a first elastic modulus and a second elastic modulus, the first elastic modulus being an elastic modulus of the material in a direction parallel to the fiber orientation, the second elastic modulus being an elastic modulus of the material in a direction orthogonal to the fiber orientation;

selecting a reference direction; and determining the elastic modulus of each element so that the first elastic modulus is determined as the elastic modulus of the element when the reference direction is parallel to the fiber orientation of the element, the second elastic modulus is determined as the elastic modulus of the element when the reference direction is orthogonal to the fiber orientation of the element, and the elastic modulus of the element is determined as a function of the angle between the fiber orientation of the element and the reference direction when the desired direction is neither parallel nor orthogonal to the fiber orientation of the element.

12. The electronic computer memory according to claim 11, wherein the elastic modulus of the element is determined using the following equation:

$$C = \sqrt{A^2\cos^2\theta + B^2\sin^2\theta} \quad,$$

where C is the elastic modulus of the element, A is the first elastic modulus, B is the second elastic modulus, and $\theta$ is the angle between the fiber orientation of the element and the reference direction.

13. An electronic computer system for determining an elastic modulus of each element of a plurality of elements representing a material including fibers in a desired direction, comprising:

means for representing a fiber orientation of each element; and means for determining the elastic modulus of each element based on a first elastic modulus, a second elastic modulus and an angle between the fiber orientation of the element and the desired direction, the first elastic modulus being an elastic modulus of the material in a direction parallel to the fiber orientation, the second elastic modulus being an elastic modulus of the material in a direction orthogonal to the fiber orientation.

14. The electronic computer system according to claim 13, further comprising means for sequentially selecting an element from the elements and determining the elastic modulus of a selected element until all the elements are selected.

15. The electronic computer system according to claim 14, further comprising means for storing the elastic modulus of each element of the material for use in structural analysis of the material.

16. The electronic computer system according to claim 13, wherein the means for representing the fiber orientation of the material is based on flow simulation of molten material including the fibers flowing into a mold.

17. The electronic computer system according to claim 13, wherein the means for determining the elastic modulus determines the first elastic modulus as the elastic modulus of the element when the desired direction is parallel to the fiber orientation of the element, determines the second elastic modulus as the elastic modulus of the element when the desired direction is orthogonal to the fiber orientation of the element, and determines the elastic modulus of the element as a function of the angle between the fiber orientation of the element and the desired direction when the desired direction is neither parallel nor orthogonal to the fiber orientation of the element.

18. The electronic computer system according to claim 17, wherein the means for determining the elastic modulus of the element is determined using the following equation:

$$C = \sqrt{A^2\cos^2\theta + B^2\sin^2\theta} \quad,$$

where C is the elastic modulus of the element, A is the first elastic modulus, B is the second elastic modulus, and $\theta$ is the angle between the fiber orientation of the element and the desired direction.

19. The electronic computer system according to claim 15, further comprising means for performing the structural analysis of the material.

20. The electronic computer system according to claim 16, further comprising means for simulating flow of molten material including the fibers flowing into the mold.

* * * * *